United States Patent
Yeh

(10) Patent No.: US 6,498,644 B1
(45) Date of Patent: Dec. 24, 2002

(54) ALIGNMENT SYSTEM OF WAFER STAGE

(75) Inventor: Chin-Teh Yeh, Taipei (TW)

(73) Assignees: Promos Technologies Inc., Hsinchu (TW); Mosel Vitelic Inc., Hsinchi (TW); Siemens AG, Munich (DE)

( * ) Notice: Subject to any disclaimer, the term of this patent is extended or adjusted under 35 U.S.C. 154(b) by 0 days.

(21) Appl. No.: 09/395,429

(22) Filed: Sep. 14, 1999

Related U.S. Application Data

(63) Continuation-in-part of application No. 08/932,391, filed on Sep. 17, 1997, now Pat. No. 5,972,887.

(51) Int. Cl.$^7$ .................................................. G01B 11/00
(52) U.S. Cl. ....................................... 356/401; 356/399
(58) Field of Search ................................ 356/399, 400, 356/401

(56) References Cited

U.S. PATENT DOCUMENTS 4,200,395 A * 4/1980 Smith et al. ................. 250/550

* cited by examiner

Primary Examiner—Frank G. Font
Assistant Examiner—Andrew H. Lee
(74) Attorney, Agent, or Firm—J.C. Patents

(57) ABSTRACT

An alignment system and method for a wafer stage. A chopper is used. A wafer stage is disposed at one side of the chopper, while a detector is disposed at the other side of the chopper. The chopper is rotating with a constant angular frequency. The detector is to detect the wafer stage, while the wafer stage is covered by the blade of the chopper, the measured signal is zero, while the wafer stage is not covered by the bladed and is detected by the detector, a signal is obtained. Therefore, a duty cycle and a phase can be read from the detector. Thus, with a constant rotating angular frequency, an actual position of the measured object can be obtained to align the wafer stage.

10 Claims, 2 Drawing Sheets

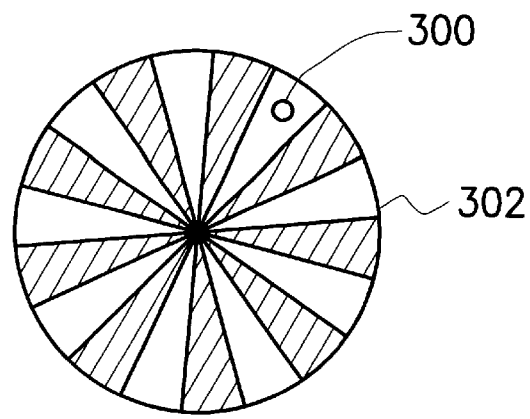
FIG. 3a
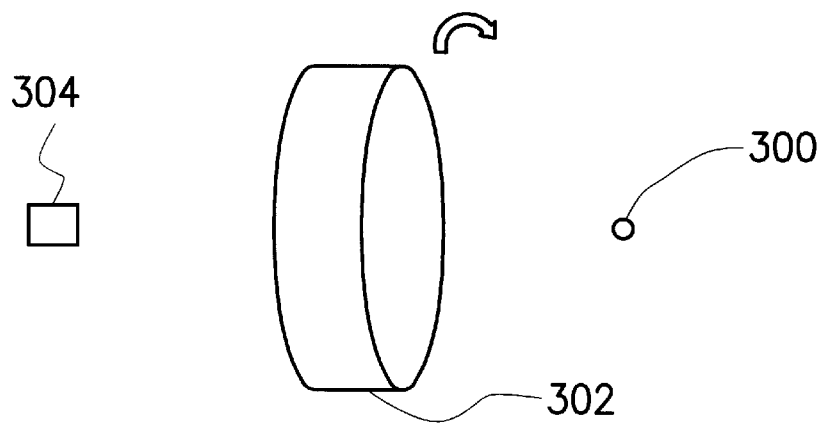
FIG. 3b
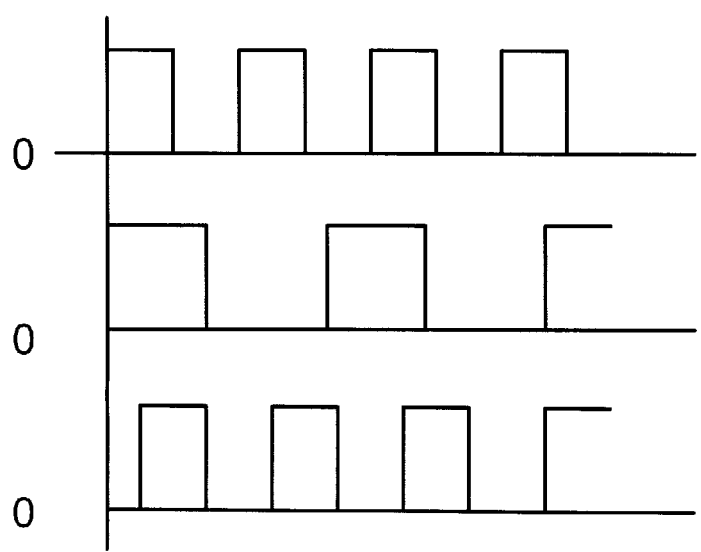
FIG. 4a
FIG. 4b
FIG. 4c

ALIGNMENT SYSTEM OF WAFER STAGE

This application is a continuation-in-part of application Ser. No. 08/932,391, filed on Sep. 17, 1997, now U.S. Pat. No. 5,972,887.

BACKGROUND OF THE INVENTION

1. Field of the Invention

The invention relates in general to a stepper and a method used for an alignment of positions of a wafer stage or a wafer on the wafer stage. More particularly, the invention relates to an alignment system and method using a chopper instead of an interferometer.

2. Description of the Related Art

In a semiconductor fabrication process, photolithography process plays an important role for further reduction of dimensions of devices and higher integration of more and more devices. In the photolithography process, whether the wafer stage or the wafer on the wafer stage is precisely aligned directly determined the precision of pattern, and thus, determines the quality of devices. In a currently widely used stepper, some sub-systems such as wafer stage, alignment system, illuminator and lens determine the performance of the stepper, and consequently, determine the properties and characteristics of the end products.

A typical stepper has a high speed stage that "steps" the wafer precisely with respect to the imaging optics and the IC reticles (photomask), moving the distances necessary to exactly repeat the image field in a Cartesian grid and thus fill the wafer surface. In the typical reduction stepper the stage travels in the horizontal plane underneath a fixed, vertically mounted lens. Once the wafer is placed on the exposure chuck and stepped under the lens, it is aligned by automatic systems that detect wafer targets optically and move the stage in small increments to correct the wafer position with respect to the ideal image field. The wafer is also positioned in vertical axis by autofocus systems, which in modern steppers also include the capability to pivot the vacuum chuck that holds the wafer during exposure in order to reduce any net tilt in the wafer surface due to chuck or wafer flatness errors.

FIG. 1 shows a conventional technique that employing heterodyne Interferometer to measure the position of the wafer stage. A laser beam emitted from a laser light source 102 reaches a beam splitter 108. Ideally, half portion of the laser beam passes through the beam splitter 108, while the other half portion of the laser beam is reflected to a reference mirror 106. These two beams then merge onto a detector 104. The combination of these two beams is either a result of constructive interference or a destructive interference, depending on the phase of the beams. The intensity of the signal detected by the detector 104 reflects the position of the wafer stage 100. The shifting direction of the wafer stage 100 can be obtained from the light reflected by the stage mirror according to the theory of Doppler Shift.

In addition, by installing one heterodyne interferometer at each direction such as X-axis, Y-axis and Z-axis can thus measure the displacement or rotation of the stage.

In the above conventional design of alignment system for wafer stage, the precision of the interferometers is prominently affected by vibration, stability of light source and fluctuation of power source. Especially for scanning the photomask and wafer, the control of vibration is the major factor to determine the throughput of the stepper.

SUMMARY OF THE INVENTION

The invention provides an alignment system for a wafer stage. A chopper is placed between the wafer stage and a detector. The wafer stage is placed within the scanning coverage of the chopper, while the detector measures a duty cycle and a phase of observation of the object at the other side of the chopper. According to the measured duty cycle, whether the wafer stage is aligned can be determined. This alignment system is not affected by vibration and the stability of light source or power source. Therefore, even the vibration of the wafer stage or the system is serious or the light source or power source is unstable, the position of wafer stage can be precisely corrected.

Thus, by employing the alignment system mentioned above, a method of precisely aligning a wafer stage is further provided. A wafer stage which may include an alignment mark thereon is provided. A chopper is placed on top of the wafer stage, or more specifically, on top of the alignment mark on the wafer stage, while the wafer stage of the alignment or object on the wafer stage to be aligned is within coverage of the chopper. The chopper is rotating with a constant speed, while a detector is disposed behind the chopper. The duty cycle and the phase for observing the wafer stage in front of the chopper are read by the detector. While the duty cycle and phase read from the detector are not consistent with a predetermined duty cycle when the wafer stage is precisely aligned, according to the difference of the duty cycle and phase, the exact positions of the wafer stage can be obtained.

Both the foregoing general description and the following detailed description are exemplary and explanatory only and are not restrictive of the invention, as claimed.

BRIEF DESCRIPTION OF THE DRAWINGS

FIG. 3a illustrates a chopper used in an alignment system of a wafer stage according to the invention;

FIG. 3b shows an embodiment of an alignment system of a wafer stage according to the invention; and FIG. 4a to FIG. 4c shows the duty cycles of different positions of measured object.

DESCRIPTION OF THE PREFERRED EMBODIMENTS

Figure 1:
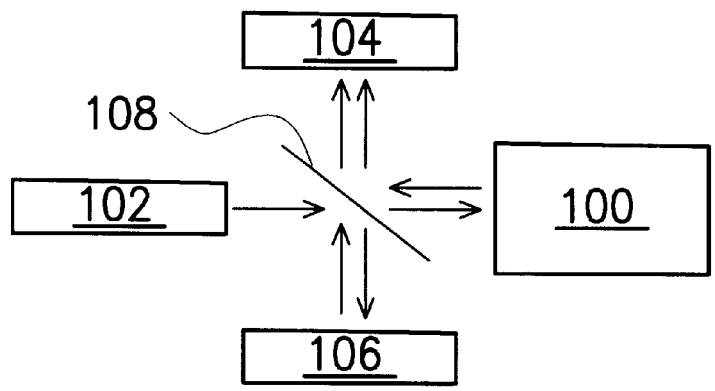
FIG. 1 shows a conventional alignment system of a wafer stage.
Figure 2:
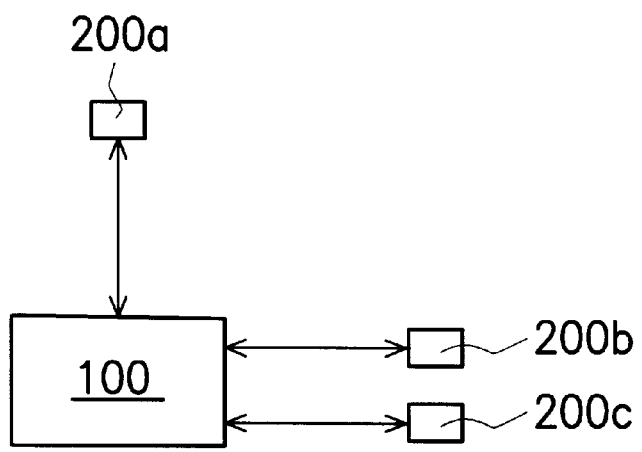
FIG. 2 shows a conventional alignment system of a wafer stage with a function that can perform alignment in three directions.

FIG. 3a shows a chopper used in one embodiment according to the invention, while FIG. 3b shows an alignment system used for a wafer stage. As shown in FIG. 3a, a chopper 302 is used in the invention. The dimension and the number of the blades are various and dependent on specific requirements. One requirement of the dimension of the chopper 302 is that the scanning coverage should include the object to be measured or to be detected. For a commonly used wafer stage and wafer in manufacture lately, the diameter of the chopper 302 can be about 200 millimeters. Regarding to the number of blades, it can vary from one to multiple blades. In FIG. 3a, the chopper 302 with eight blades is illustrated as an example. When an object 300 is disposed at one side of the chopper 302, viewing from the other side of the chopper 302, the object 300 can be observed interstitially. That is, there is a duty cycle of the observation for the object 300 from the other side of the chopper 302. While the chopper 302 is rotating with a constant angular frequency $\omega$, the frequency to observe the object 300 at the other side of the chopper 302 thus has a constant duty cycle.

Apart from the angular frequency ω of the chopper 302, the position of the object 300 also affects the resultant duty cycle. For example, when the object 300 is disposed deviated from the central axis direction of the chopper 302, the duty cycle to observe the object 300 is changed. Therefore, according to the duty cycle, the position of the object 300 can be measured. That is, while a displacement of the object occurs, it can be monitored by the measured duty cycle of the chopper 302. In contrast, when an azimuth of the object 300 is varied, the phase change directly reflects the variation.

Referring to FIG. 3b, an object 300, for example, a wafer stage, an alignment mark on a wafer stage, or even a wafer, is placed at one side of a chopper 302 within the scanning coverage of the chopper 302. The chopper 302 comprises at least one blade, and very often, more than one blade. At the other side of the chopper 302, a detector 304 is disposed for detecting the existence of the object 300. While the object 300 is covered by one blade of the chopper 302, the detector 304 detects nothing, so that referring to FIG. 4a to FIG. 4b, the signal intensity is zero. In contrast, while the chopper 302 rotates to a state that the object 300 is not covered by one of the blades thereof, the detector 304 detects a signal with an intensity as shown in FIG. 4a to FIG. 4c.

Assuming that the object 300 is precisely aligned without being shifted, with a constant angular speed of the chopper 302, a duty cycle read from the detector 304 is constant as shown in FIG. 4a. When the object 300 is shifted inwardly with respect to the center axis direction of the chopper 300, a duty cycle read from the detector 304 is shown as FIG. 4b. In contrast; when the object 300 is shifted tangentially or in angular position with respect to the central axis of the chopper 300, a duty cycle read from the detector 304 is shown as FIG. 4c. By the difference of the read duty cycles from the detector 304, whether a wafer stage, an alignment on the wafer stage or a wafer is precisely aligned can be determined without being affected by factors such as vibration; stability of light source or power source.

Thus, the invention provides a chopper disposed in front of a wafer stage with a scanning coverage which can cover the dimension of the wafer stage, or an alignment mark on the wafer stage. At the other side of the chopper, a detector is disposed and aligned with the object to be measured or observed. Detected by the detector, a signal is obtain interstitially to result in a duty cycle. Providing a predetermined duty cycle while the wafer stage is precisely aligned, while reading a duty cycle deviating from the predetermined one, the wafer stage is to be moved, that is, the position of the wafer stage is to be adjusted until it is precisely aligned.

Other embodiments of the invention will appear to those skilled in the art from consideration of the specification and practice of the invention disclosed herein. It is intended that the specification and examples to be considered as exemplary only, with a true scope and spirit of the invention being indicated by the following claims.

What is claimed is:

1. An alignment system of a wafer stage, comprising:
   an alignment mark on the wafer stage, wherein the wafer stage includes a wafer;
   a detector, located at one side of the wafer stage for observing the alignment mark; and
   a chopper, located between the detector and the alignment mark, wherein the chopper includes at least one blade, and a blade side of each the at least one blade has a line shape, so as to produce a different duty cycle when a position of the alignment mark is shifted along a radial direction of the chopper.

2. The alignment system according to claim 1, wherein the chopper comprises a plurality of blades, each of which is equally distant from the other.

3. The alignment system according to claim 1, wherein the chopper has a diameters of about 200 millimeters.

4. The alignment system according to claim 1, wherein the chopper has a scanning coverage which cover a range to be measured of the wafer stage.

5. An alignment method of a wafer stage, comprising:
   providing the wafer stage;
   providing a chopper on top of the wafer stage, the chopper rotating with a constant angular frequency;
   providing a predetermined duty cycle and phase of observing the wafer stage while the wafer stage is precisely aligned; and
   measuring an actual duty cycle and phase for observing the wafer stage via the chopper, and determine an actual position of the wafer stage according to a difference between the predetermined and actual duty cycle and phase.

6. The method according to claim 5, wherein in the step of measuring the actual duty cycle, a detector is used to observed wafer stage via the chopper.

7. The method according to claim 5, wherein the chopper comprises at least one blade.

8. The method according to claimed 5, wherein the chopper comprises a plurality of blades, which are evenly distributed in polar angle.

9. The method according to claim 5, wherein the chopper has a diameter of about 200 millimeter.

10. The method according to claim 5, wherein the chopper has a scanning coverage fully covers a range to be measured of the wafer stage.

* * * * *

UNITED STATES PATENT AND TRADEMARK OFFICE
CERTIFICATE OF CORRECTION

PATENT NO.     : 6,498,644 B1
DATED          : December 24, 2002
INVENTOR(S)    : Chin-Teh Yeh It is certified that error appears in the above-identified patent and that said Letters Patent is hereby corrected as shown below:

The title page should be deleted and substitute therefore the attached title page.

Delete Figures 3a and 4b and substitute therefore Figs. 3a and 4b as shown on the attached page.

Signed and Sealed this

Ninth Day of September, 2003

JAMES E. ROGAN
*Director of the United States Patent and Trademark Office*

(12) United States Patent
Yeh

(10) Patent No.: US 6,498,644 B1
(45) Date of Patent: Dec. 24, 2002

(54) ALIGNMENT SYSTEM OF WAFER STAGE

(75) Inventor: Chin-Teh Yeh, Taipei (TW)

(73) Assignees: Promos Technologies Inc., Hsinchu (TW); Mosel Vitelic Inc., Hsinchi (TW); Siemens AG, Munich (DE)

(*) Notice: Subject to any disclaimer, the term of this patent is extended or adjusted under 35 U.S.C. 154(b) by 0 days.

(21) Appl. No.: 09/395,429

(22) Filed: Sep. 14, 1999

Related U.S. Application Data

(63) Continuation-in-part of application No. 08/932,391, filed on Sep. 17, 1997, now Pat. No. 5,972,887.

(51) Int. Cl.$^7$ .................................................. G01B 11/00
(52) U.S. Cl. ........................................ 356/401; 356/399
(58) Field of Search .............................. 356/399, 400, 356/401

(56) References Cited

U.S. PATENT DOCUMENTS 4,200,395 A * 4/1980 Smith et al. ............... 250/550

* cited by examiner

Primary Examiner—Frank G. Font
Assistant Examiner—Andrew H. Lee
(74) Attorney, Agent, or Firm—J.C. Patents

(57) ABSTRACT

An alignment system and method for a wafer stage. A chopper is used. A wafer stage is disposed at one side of the chopper, while a detector is disposed at the other side of the chopper. The chopper is rotating with a constant angular frequency. The detector is to detect the wafer stage, while the wafer stage is covered by the blade of the chopper, the measured signal is zero, while the wafer stage is not covered by the bladed and is detected by the detector, a signal is obtained. Therefore, a duty cycle and a phase can be read from the detector. Thus, with a constant rotating angular frequency, an actual position of the measured object can be obtained to align the wafer stage.

10 Claims, 2 Drawing Sheets

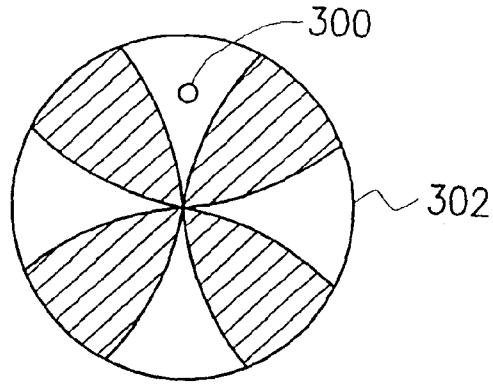

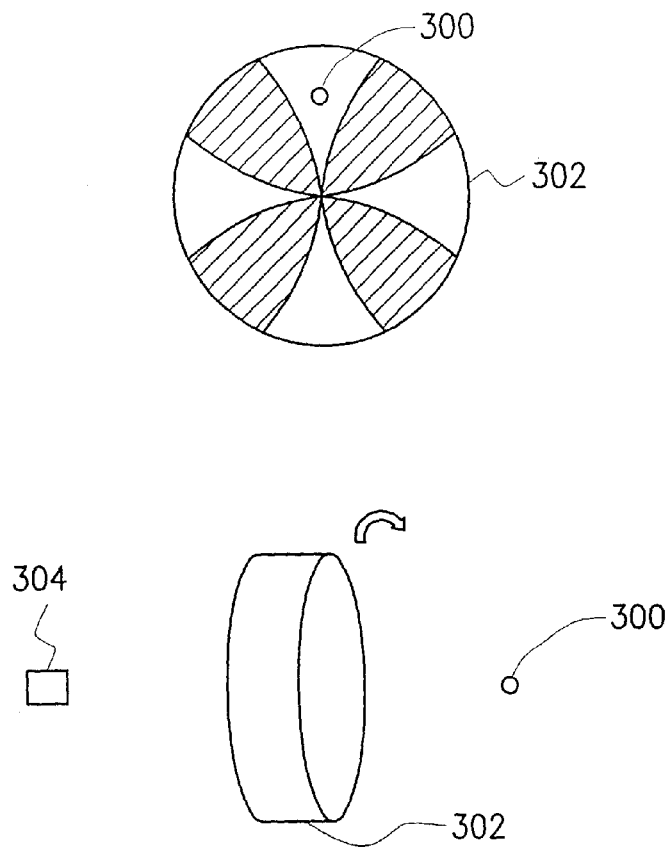
FIG. 3b
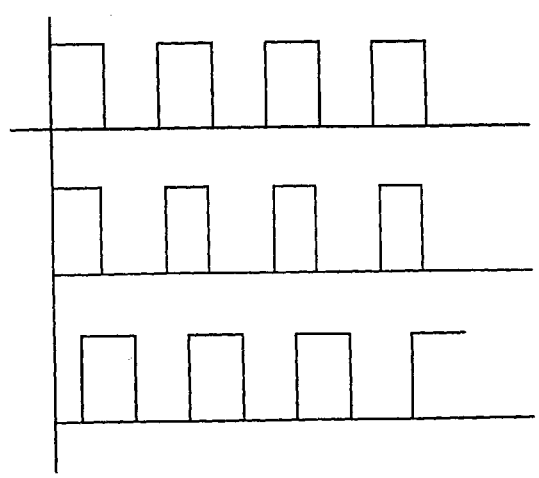
FIG. 4a
FIG. 4b
FIG. 4c